United States Patent
Meilander et al.

(10) Patent No.: US 8,216,523 B2
(45) Date of Patent: Jul. 10, 2012

(54) DECONTAMINATION UNIT WITH COLLAPSIBLE DECONTAMINATION ENCLOSURE AND DECONTAMINATION PROCESS

(75) Inventors: Timothy W. Meilander, Broadview Heights, OH (US); Paul A Wiget, Mentor, OH (US); Jain F. McVey, Lakewood, OH (US); Mark E. Pasmore, Madison, OH (US); Janusz K. Kozak, Columbia, MD (US); Michael A. Centanni, Parma, OH (US)

(73) Assignee: STERIS Inc., Temecula, CA (US)

( * ) Notice: Subject to any disclaimer, the term of this patent is extended or adjusted under 35 U.S.C. 154(b) by 448 days.

(21) Appl. No.: 12/033,897

(22) Filed: Feb. 20, 2008

(65) Prior Publication Data
US 2008/0279720 A1 Nov. 13, 2008

Related U.S. Application Data

(60) Provisional application No. 60/893,134, filed on Mar. 6, 2007, provisional application No. 60/962,876, filed on Aug. 1, 2007.

(51) Int. Cl.
*A61L 9/00* (2006.01)
*B01D 1/00* (2006.01)
*B01D 3/00* (2006.01)
*B01D 17/00* (2006.01)

(52) U.S. Cl. .......................... 422/294; 422/30
(58) Field of Classification Search .................. 422/30, 422/294
See application file for complete search history.

(56) References Cited

U.S. PATENT DOCUMENTS

| | | | |
|---|---|---|---|
| 2,348,574 A | 5/1944 | Ross | 21/96 |
| 2,823,863 A | 2/1958 | Moyes | 237/2 |
| 3,713,383 A | 1/1973 | Crescenzo et al. | 102/6 |
| 3,858,645 A | 1/1975 | Egger | 165/66 |
| 3,994,684 A | 11/1976 | Tomasulo | 21/91 |
| 4,675,923 A | 6/1987 | Ashley | 4/599 |
| 4,808,377 A | 2/1989 | Childers et al. | 422/26 |
| 4,858,256 A | 8/1989 | Shankman | 4/597 |
| 4,861,560 A | 8/1989 | Nakajima | 422/111 |
| 4,909,988 A | 3/1990 | Childers et al. | 422/26 |
| 4,909,999 A * | 3/1990 | Cummings et al. | 422/298 |
| 4,993,199 A | 2/1991 | Hughes | 51/426 |

(Continued)

FOREIGN PATENT DOCUMENTS

DE 19506200 2/1995

(Continued)

OTHER PUBLICATIONS

International Search Report and Written Opinion, Application No. PCT/US2008/054338, mailed Oct. 6, 2008.

*Primary Examiner* — Walter D Griffin
*Assistant Examiner* — Christopher Vandeusen
(74) *Attorney, Agent, or Firm* — Renner, Otto, Boisselle & Sklar, LLP

(57) ABSTRACT

The disclosed invention relates to a decontamination unit that employs a collapsible decontamination enclosure and a decontaminant air stream generator that uses catalytic discharge. The invention also relates to a decontamination process using the decontamination unit. The decontamination unit may be carried by an individual person, for example, in the form of a backpack. The decontamination unit may be ruggedized for use in hostile environments such as those that may be anticipated for military applications.

21 Claims, 3 Drawing Sheets

U.S. PATENT DOCUMENTS

| | | | |
|---|---|---|---|
| 5,037,623 A | 8/1991 | Schneider et al. | 422/292 |
| 5,061,235 A | 10/1991 | Hogan | 600/21 |
| 5,114,670 A | 5/1992 | Duffey | 422/24 |
| 5,258,162 A | 11/1993 | Andersson et al. | 422/28 |
| 5,277,875 A | 1/1994 | Albright et al. | 422/109 |
| 5,286,447 A | 2/1994 | Fannin et al. | 422/28 |
| 5,331,991 A | 7/1994 | Nilsson | 135/93 |
| 5,405,587 A | 4/1995 | Fernandez et al. | 422/292 |
| 5,472,004 A | 12/1995 | Gilliard | 134/111 |
| 5,502,975 A | 4/1996 | Brickley et al. | 62/94 |
| 5,520,893 A | 5/1996 | Kasting, Jr. et al. | 422/305 |
| 5,634,880 A | 6/1997 | Feldman et al. | 600/132 |
| 5,665,316 A | 9/1997 | Salonia et al. | 422/113 |
| 5,706,846 A | 1/1998 | Sutton | 135/128 |
| 5,868,667 A | 2/1999 | Lin et al. | 600/133 |
| 5,882,590 A | 3/1999 | Stewart et al. | 422/28 |
| 5,916,096 A | 6/1999 | Wiesmann et al. | 52/63 |
| 5,958,336 A | 9/1999 | Duarte | 422/24 |
| 6,077,480 A | 6/2000 | Edwards et al. | 422/28 |
| 6,096,265 A | 8/2000 | Mezger et al. | |
| 6,120,739 A | 9/2000 | Thomas et al. | 422/186.07 |
| 6,199,388 B1 | 3/2001 | Fischer, Jr. | 62/90 |
| 6,488,902 B1 | 12/2002 | DeCato et al. | 423/210 |
| 6,517,639 B2 | 2/2003 | Toepfer et al. | 134/21 |
| 6,532,741 B2 | 3/2003 | Watkins | 60/723 |
| 6,557,365 B2 | 5/2003 | Dinnage et al. | 62/94 |
| 6,645,450 B2 | 11/2003 | Stoltz et al. | 423/245.2 |
| 6,652,248 B2 | 11/2003 | Watkins et al. | 417/381 |
| 6,711,907 B2 | 3/2004 | Dinnage et al. | 62/94 |
| 6,734,405 B2 | 5/2004 | Centanni et al. | 219/628 |
| 6,751,964 B2 | 6/2004 | Fischer | 62/94 |
| 6,834,494 B2 | 12/2004 | Lohner et al. | 60/218 |
| 6,852,279 B2 | 2/2005 | Williams et al. | 422/4 |
| 6,867,393 B1 | 3/2005 | Lewis | 219/401 |
| 6,887,821 B2 | 5/2005 | Mays et al. | 502/202 |
| 6,906,296 B2 | 6/2005 | Centanni et al. | 219/628 |
| 6,923,716 B2 | 8/2005 | Koeger | 454/230 |
| 6,928,143 B2 | 8/2005 | Menear et al. | 378/69 |
| 6,936,434 B2 | 8/2005 | McDonnell et al. | 435/31 |
| 6,953,549 B2 | 10/2005 | Hill et al. | 422/30 |
| 6,986,386 B2 | 1/2006 | Sekhar et al. | 165/214 |
| 7,047,751 B2 | 5/2006 | Dinnage et al. | 62/94 |
| 7,102,052 B2 | 9/2006 | McVey et al. | 588/303 |
| 7,144,550 B2 | 12/2006 | Devine et al. | 422/28 |
| 7,145,052 B1 | 12/2006 | Watkins | 588/320 |
| 7,160,566 B2 | 1/2007 | Fink et al. | 426/235 |
| 7,203,979 B2 | 4/2007 | O'Brien | 4/900 |
| 7,308,798 B2 | 12/2007 | Caggiano | 62/63 |
| 2002/0015672 A1 | 2/2002 | Saint-Martin et al. | 422/295 |
| 2003/0051462 A1 | 3/2003 | Watkins | 60/204 |
| 2003/0129111 A1 | 7/2003 | Miller et al. | 422/292 |
| 2003/0138347 A1 | 7/2003 | Lin | 422/28 |
| 2003/0164091 A1 | 9/2003 | Hill et al. | 95/90 |
| 2003/0230567 A1* | 12/2003 | Centanni et al. | 219/628 |
| 2004/0057868 A1* | 3/2004 | McVey et al. | 422/28 |
| 2004/0071587 A1* | 4/2004 | McAtarian | 422/1 |
| 2004/0184950 A1 | 9/2004 | McVey et al. | 422/4 |
| 2004/0197252 A1 | 10/2004 | Parrish | 423/235 |
| 2004/0241065 A1* | 12/2004 | Kampa et al. | 422/305 |
| 2005/0005533 A1 | 1/2005 | Stewart et al. | 52/79.1 |
| 2005/0220666 A1 | 10/2005 | Foster | 422/28 |
| 2005/0279047 A1 | 12/2005 | Kalnay | 52/641 |
| 2006/0008379 A1 | 1/2006 | Mielnik et al. | 422/32 |
| 2006/0018788 A1 | 1/2006 | Monico et al. | 422/26 |
| 2006/0088441 A1 | 4/2006 | Hill | |
| 2006/0099121 A1 | 5/2006 | Doona et al. | 422/292 |
| 2006/0252974 A1 | 11/2006 | McVey et al. | 588/299 |
| 2006/0270887 A1 | 11/2006 | Watkins | 588/300 |
| 2007/0098592 A1 | 5/2007 | Buczynski et al. | 422/3 |
| 2007/0274858 A1 | 11/2007 | Childers et al. | 422/28 |

FOREIGN PATENT DOCUMENTS

| | | |
|---|---|---|
| EP | 1607106 | 5/2005 |
| FR | 2515408 | 10/1981 |
| WO | 00/57929 | 5/2000 |
| WO | 02/066082 A1 | 8/2002 |
| WO | 2004035094 | 4/2004 |
| WO | 2007102798 | 9/2007 |

\* cited by examiner

DECONTAMINATION UNIT WITH COLLAPSIBLE DECONTAMINATION ENCLOSURE AND DECONTAMINATION PROCESS

This application claims benefit under 35 U.S.C. §119(e) to U.S. Provisional Application Ser. No. 60/893,134, filed Mar. 6, 2007, and U.S. Provisional Application Ser. No. 60/962, 876, filed Aug. 1, 2007. These applications are incorporated herein by reference in their entireties.

TECHNICAL FIELD

This invention relates to a decontamination unit equipped with a collapsible decontamination enclosure and to a decontamination process using the decontamination unit.

BACKGROUND

Decontaminant generating systems, such as those used to generate vaporous hydrogen peroxide (VHP), have been used to decontaminate large enclosures such as rooms and buildings (e.g., hotel rooms, hospital wards, scientific laboratories, etc.) from contaminants such as bacteria, molds, fungi, yeasts, and the like.

SUMMARY

It would be advantageous for the military to use these decontaminant systems in the field for defense against chemical and biological weapons. However, there are situations in the field where, due to the terrain or remoteness of the location, it is not possible to transport these systems to the field location. This invention provides a solution to this problem. With the inventive decontamination unit an individual person may carry the unit to the desired location. This is due to the fact that the inventive decontamination unit is lightweight and employs a decontamination enclosure that is collapsible and may be carried as part of a backpack. Also, the decontaminant air stream generator employed with the decontamination unit uses catalytic discharge to vaporize liquid hydrogen peroxide and thus does not require an electric generator to provide electric input.

This invention relates to a decontamination unit, comprising: a collapsible enclosure equipped with a gas inlet and a gas outlet, the collapsible enclosure when erected being suitable for providing a decontamination enclosure for containing articles to be decontaminated, the collapsible enclosure when collapsed being suitable for being transported; a decontaminant air stream generator adapted for containing liquid hydrogen peroxide, the generator being adapted for catalytically converting part of the liquid hydrogen peroxide to water and oxygen in an exothermic reaction and for vaporizing part of the liquid hydrogen peroxide to form vaporous hydrogen peroxide, the generator including an inlet adapted for permitting air to flow into the generator in contact with the vaporous hydrogen peroxide and an outlet adapted for permitting a decontaminant air stream comprising the air and vaporous hydrogen peroxide to flow out of the generator; a blower adapted to be connected to the generator outlet and the collapsible enclosure gas inlet, the blower being suitable for forcing the flow of the decontaminant air stream from the generator into the collapsible enclosure; and an exhaust hose adapted to be attached to the collapsible enclosure gas outlet, the exhaust hose comprising an interior wall impregnated with a catalyst for converting hydrogen peroxide to water and oxygen, and/or the exhaust hose comprising a biological and/ or chemical hazard filter.

This invention relates to a process for operating the foregoing decontamination unit which may comprise: erecting the collapsible enclosure to form a decontamination enclosure suitable for receiving articles to be decontaminated; connecting the blower to the gas inlet of the enclosure; connecting the blower to the generator; connecting the exhaust hose to the gas outlet of the enclosure; placing one or more contaminated articles in the enclosure; generating a decontaminant air stream comprising air and vaporous hydrogen peroxide in the generator; flowing the decontaminant air stream into the enclosure; contacting the contaminated articles in the enclosure with the decontaminant air stream to decontaminate the contaminated articles; flowing gas from the enclosure through the exhaust hose; opening the enclosure; and removing decontaminated articles from the enclosure.

BRIEF DESCRIPTION OF THE DRAWINGS

In the annexed drawings all parts and features have like references. A number of the annexed drawings are schematic illustrations which are not necessarily proportioned accurately or drawn to scale.

DETAILED DESCRIPTION

All ranges and ratio limits disclosed in the specification and claims may be combined in any manner. It is to be understood that unless specifically stated otherwise, references to "a", "an", and/or "the" may include one or more than one, and that reference to an item in the singular may also include the item in the plural. All combinations specified in the claims may be combined in any manner.

The term "ruggedized," and like terms such as "ruggedization," are used herein to refer to apparatus that is: (1) hardened to ensure that five exposures to chemical, biological, radiological or nuclear (CBRN) contaminants, decontaminants and decontaminating procedures over a thirty-day period do not cause the apparatus to require corrective maintenance during that thirty-day period; (2) capable of being used at temperatures ranging from about −32° C. to about 49° C.; (3) capable of being used in relative humidities ranging from about 5% to about 100%; and/or (4) capable of operating when exposed to conventional hazards of solar radiation, rain, fungus, salt, fog, sand, dust, vibration and/or shock in accordance with Military Standard 810 (MIL-STD-810).

The term "conduit" may refer to any conduit for conveying a fluid. The conduits disclosed herein may be in any desired form. For example, the conduits may be flexible hoses, pipes, tubings, channels, and the like. These may be made of materials sufficient to provide the required properties of strength, flexibility, and resistance to the fluids being conveyed. The conduits may be ruggedized to permit use in hostile environments such as those that may be encountered in military applications.

The term "fluid" may refer to a liquid, gas, or mixture thereof.

Figure 1:
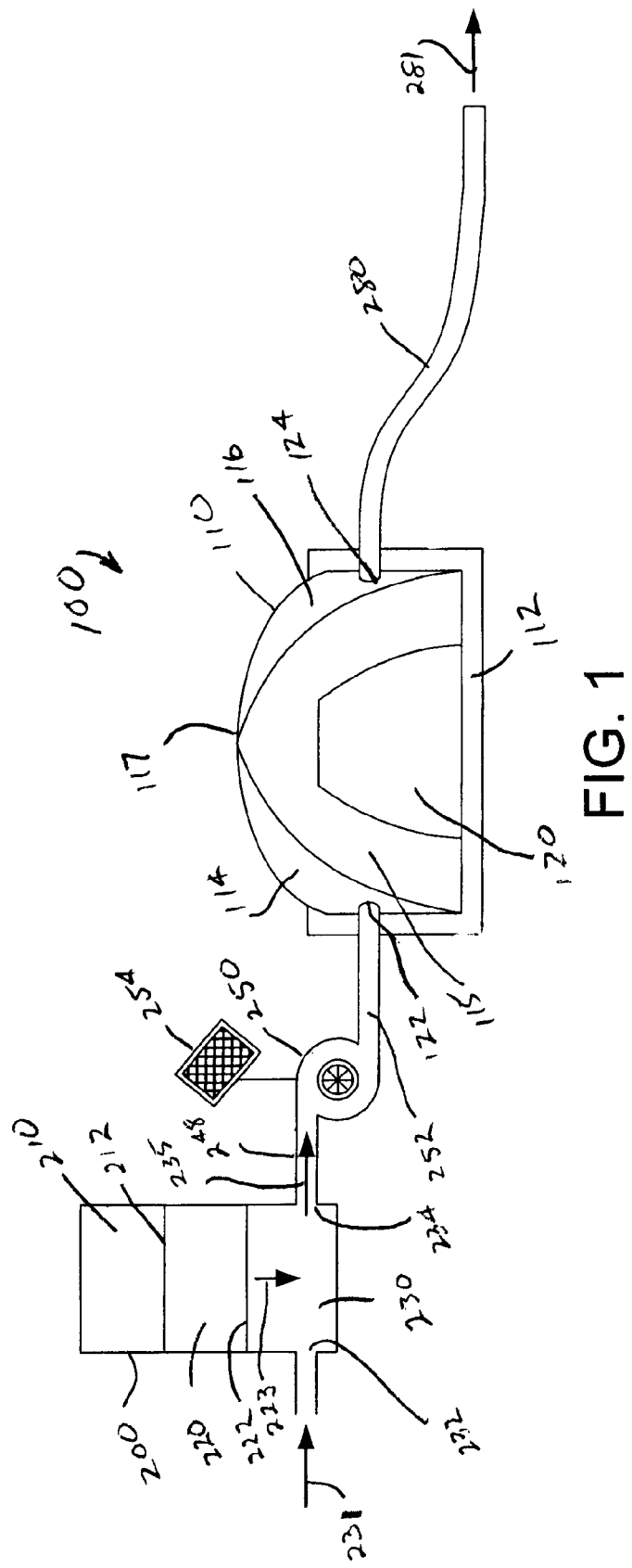
FIG. 1 is a schematic illustration of one embodiment of the inventive decontamination unit.
Figure 2:
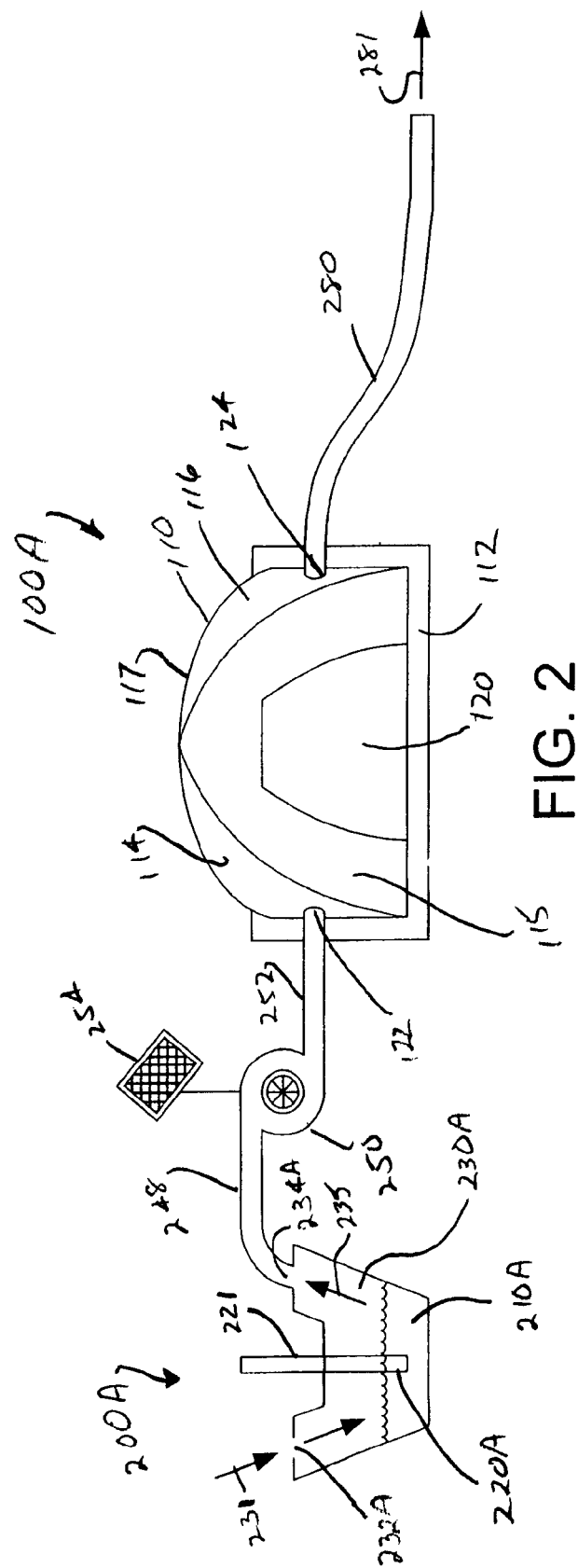
FIG. 2 is a schematic illustration of a modified embodiment of the inventive decontamination unit.

The inventive decontamination unit, in its illustrated embodiments, will be described with reference to FIGS. 1-3. Referring to FIG. 1, decontamination unit 100 may comprise collapsible enclosure 110, decontaminant air stream generator 200, blower 250, and exhaust hose 280. The decontamination unit 100A illustrated in FIG. 2 is the same as the decontamination unit 100 illustrated in FIG. 1 except that with the decontamination unit 100A, decontaminant air stream generator 200A has been substituted for the decontaminant air stream generator 200. The decontamination unit 100B illustrated in FIG. 3 is the same as the decontamination unit 100A illustrated in FIG. 2 except that with the decontamination unit 100B, gaseous ammonia container 290 has been added.

Figure 3:
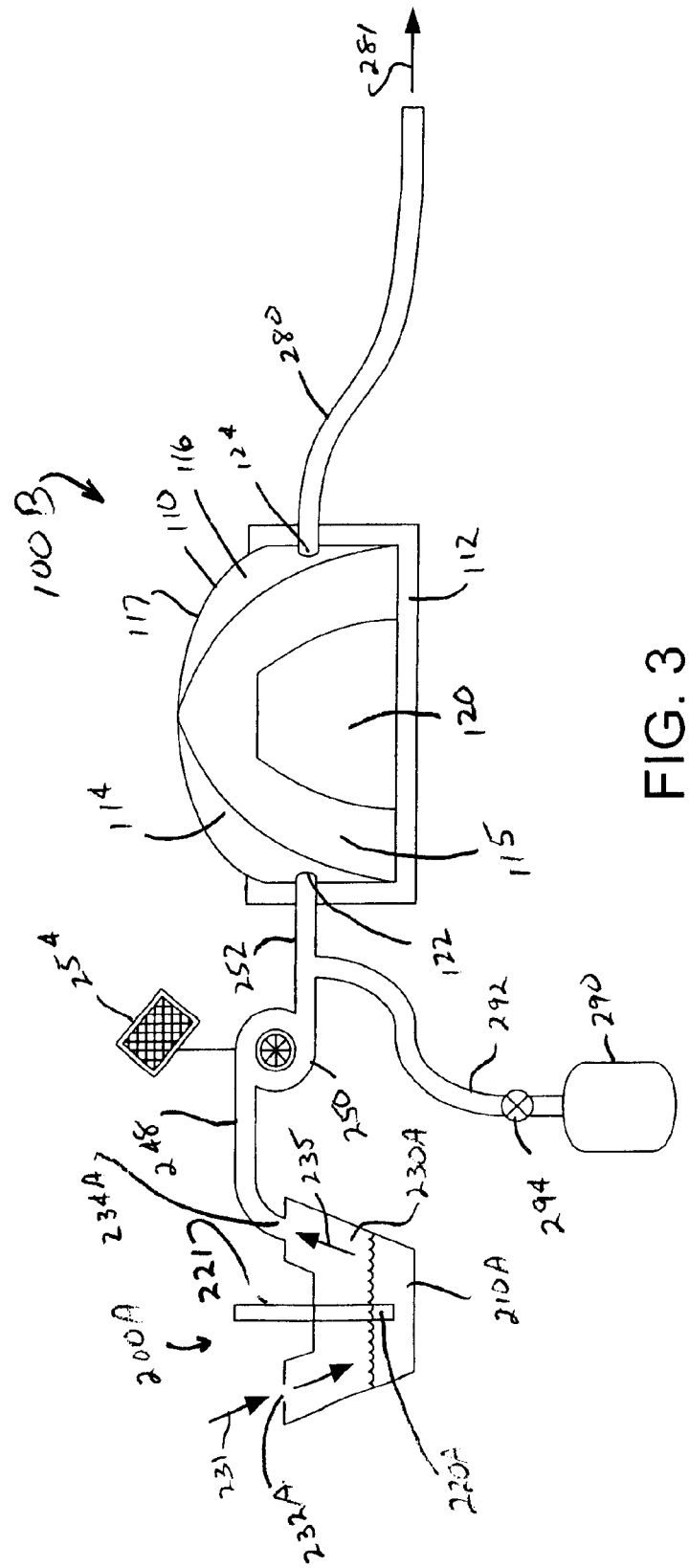
FIG. 3 is a schematic illustration of another modified embodiment of the inventive decontamination unit.

The collapsible enclosure 110, when erected as shown in FIGS. 1-3, provides a decontamination enclosure 110 suitable for receiving articles to be decontaminated. When collapsed, the collapsible enclosure 110, in combination with the other components of the decontamination unit 100, 100A or 100B, may be sufficiently compact and lightweight to be carried by an individual person. For example, the collapsed enclosure 110, in combination with the other components of the inventive decontamination unit 100, 100A or 100B, may be provided in the form of a backpack that may be facilitatingly carried to remote locations or over difficult terrain. The weight of the decontamination unit 100, 100A or 100B may be in the range up to about 40 pounds (18.1 Kg), and in one embodiment in the range from about 10 to about 40 pounds (4.5 to 18.1 Kg), and in one embodiment in the range from about 25 to about 40 pounds (11.3 to 18.1 Kg).

The collapsible enclosure 110 may include floor 112, and side walls 114, 115, 116 and 117. The collapsible enclosure 110 may include entry flap 120, gas inlet 122, and gas outlet 124. The floor, sides and entry flap of the collapsible enclosure 110 may be made of a fabric or film material that is sufficiently lightweight to permit transport and handling by an individual person, and yet be sufficiently impervious to prevent the escape of contaminate and decontaminant materials from the interior of the enclosure. The fabric or film may comprise a single ply construction or a multi-ply construction (e.g., two ply, three ply, etc.). The fabric or film materials that may be used may include natural fibers such as cotton, wool, hemp, silk, and the like, as well as synthetic fibers such as polyester, nylon, Kevlar, Mylar, vinyl (e.g., polyvinyl chloride), polypropylene, and the like. The fabric or film materials may be coated and/or impregnated with one or more suitable coating materials to enhance their resistance to the contaminate and decontaminate materials as well as any materials or conditions that the fabric or film materials may be exposed to during use. Examples of the coating materials may include vinyl coatings. The fabric or film materials may be ruggedized.

The collapsible enclosure 110 may include a collapsible interior support frame (not shown in the drawings) to support the enclosure when erected. The support frame may be made of any material that is sufficient to provide the desired properties of strength and lightweight, as well as resistance to harmful materials and conditions likely to be encountered. The support frame may be ruggedized. The support frame may be made of stainless steel, coated steel, an aluminum alloy, anodized aluminum, and the like.

The collapsible enclosure 110, when erected, may provide a decontamination enclosure 110 of sufficient scale to accommodate the needs for the desired decontamination process. The erected enclosure may have a rectangular, square or dome shape. The erected decontamination enclosure 110 may have an internal volume in the range from about 0.5 to about 30 cubic meters, and in one embodiment from in the range from about 1 to about 10 cubic meters. The erected decontamination enclosure 110 may have dimensions ranging from about 1×1×1 meters to about 3×3×3 meters. The erected decontamination enclosure 110 may be sufficiently air tight to permit operation of the decontamination process in the decontamination enclosure 110 at a slightly negative internal pressure, that is, a pressure within the decontamination enclosure in the range up to about 10 inches of water below atmospheric pressure, and in one embodiment in the range from about 0.01 to about 5 inches of water, and in one embodiment in the range from about 0.01 to about 1 inch of water, and in one embodiment in the range from about 0.01 to about 0.5 inch of water below atmospheric pressure.

The collapsible enclosure/decontamination enclosure 110 may be equipped with gas inlet 122 and gas outlet 124. The gas inlet 122 may be adapted for connection to conduit 252 which may be in the form of a flexible hose or tubing. The gas outlet 124 may be adapted for connection to exhaust hose 280. The conduit 252 may extend from the gas inlet 122 to the blower 250. The blower 250 may be adapted for connection to conduit 248. The conduit 248 may be adapted for connection to the outlet 234 of the decontaminant air stream generator 200 or the outlet 234A of the decontaminant air stream generator 200A. The conduit 248 may comprise a flexible hose or tubing. The decontaminant air stream generator 200 or the decontaminant air stream generator 200A may be used to generate the decontaminant air stream. The decontaminant air stream may flow from the decontaminant air stream generator 200 or 200A through conduit 248 to blower 250, as indicated by arrow 235, then from blower 250 through conduit 252 to gas inlet 122, and from the gas inlet 122 into the interior of the decontamination enclosure 110. The decontaminant air stream flows in the interior of the decontamination enclosure 110, contacts contaminated articles placed in the decontamination enclosure 110, and decontaminates the contaminated articles. A gaseous exhaust stream comprising spent gases (for example, air, residual hydrogen peroxide, residual hazardous biological and/or chemical materials, etc.) flows through gas outlet 124, and from gas outlet 124 into exhaust hose 280. The gaseous exhaust stream is treated in the exhaust hose 280, as discussed below, and flows out of the exhaust hose 280, as indicated by arrow 281.

The decontaminant air stream generator 200 may comprise liquid hydrogen peroxide container 210, catalyst section 220, and decontaminant air stream mixing section 230. Liquid hydrogen peroxide may be contained in the liquid hydrogen peroxide container 210 until the process for generating the decontaminant air stream is commenced. The process may be commenced by flowing the liquid hydrogen peroxide from the liquid hydrogen peroxide container 210 into the catalyst section 220. In the catalyst section 220, part but not all of the hydrogen peroxide undergoes an exothermic reaction resulting in the formation of a product composition comprising reaction products and unreacted hydrogen peroxide, the generation of heat, and an expansion of the product composition. The product composition flows from the catalyst section 220 into the decontaminant air stream mixing section 230, as indicated by arrow 223, where it is mixed with air flowing into decontaminant air stream mixing section through inlet 232, as indicated by arrow 231, to form the decontaminant air stream.

The liquid hydrogen peroxide container 210 may contain a hydrogen peroxide solution which has a relatively high concentration of hydrogen peroxide. The hydrogen peroxide concentration may be about 70% by weight or higher, and in one embodiment in the range from about 70% to about 98% by weight, and in one embodiment from about 80% to about 98%, and in one embodiment from about 85% to about 98% by weight, and in one embodiment from about 90% to about 98% by weight, and in one embodiment from about 95% to about 98% by weight, and in one embodiment the concentration may be about 98% by weight. The hydrogen peroxide solution used herein may be referred to as being a propellant grade hydrogen peroxide.

The catalyst employed in the catalyst section 220 may comprise any catalyst suitable for decomposing hydrogen peroxide. The catalyst may comprise any suitable transition metal, transition metal oxide, or combination thereof. The catalyst may comprise Ag, Mn, Pd, Pt, Rh, an oxide of one or more of the foregoing metals, or a mixture of two or more of the foregoing metals and/or oxides. The catalyst may be supported by a suitable support such as an alumina support. The catalyst may comprise silver in the form of a screen or screen plating. The catalyst may comprise a silver based alloy. The catalyst may comprise manganese dioxide. The catalyst may be in the form of a bed of particulate solids. The catalyst may be relatively undersized so as to not decompose all of the hydrogen peroxide flowing through the catalyst section 220.

The liquid hydrogen peroxide container 210 may include liquid peroxide separation wall 212 which separates the liquid hydrogen peroxide container 210 from the catalyst section 220. The liquid peroxide separation wall 212 may include one or more passageways which may be mechanically opened by the operator to permit the flow of liquid hydrogen peroxide from the liquid hydrogen peroxide container 210 into the catalyst section 220. For example, the liquid peroxide separation wall 212 may comprise two parallel plates, each containing one or more through holes. When the plates are aligned in a first position the through holes do not match up and as a result the parallel plates function as a separation wall preventing the liquid hydrogen peroxide from flowing into the catalyst section 220. One of the plates may be moved relative to the other so that the plates may become aligned in a second position wherein the through holes match up and as a result permit the liquid hydrogen peroxide to flow by force of gravity from liquid hydrogen peroxide container 210 into the catalyst section 220. Alternatively, the liquid peroxide separation wall 212 may be made of a frangible material such as glass which may be broken by the operator (for example, by using an insert rod) to permit the liquid hydrogen peroxide to flow by force of gravity from the liquid hydrogen peroxide container 210 into the catalyst section 220. Alternatively, a mechanically operated valve may be provided between the liquid hydrogen peroxide container 210 and the catalyst section 220.

The catalyst section 220 may include catalyst separation wall 222 which separates the catalyst section 220 from the decontaminant air stream mixing section 230. The catalyst separation wall 222 may include one or more openings adapted to permit the flow of the product composition from the catalyst section 220 into the decontaminant air stream mixing section 230. A pressure release valve or a pressure release membrane which may open or rupture at a predetermined pressure may be positioned in the one or more openings in the catalyst separation wall 222. The pressure release valve or pressure release membrane may be made of any suitable material that may open or rupture at the predetermined pressure. The pressure release valve or pressure release membrane may be made of a material comprising aluminized polyolefin, polyester, polytetrafluoroethylene, spun polyethylene, and the like. The pressure release valve or pressure release membrane may be adapted to open or rupture when the pressure within the catalyst section 220 resulting from the exothermic reaction of the hydrogen peroxide and the resulting expansion of the product composition exceeds a predetermined value. This predetermined value may be a gauge pressure in the range from about 2 to about 100 pounds per square inch (psi) (0.14 to 6.80 atmospheres), and in one embodiment from about 40 to about 80 psi (2.72 to 5.44 atmospheres). When the pressure release valve or pressure release membrane opens or ruptures, the product composition formed by the exothermic reaction of the hydrogen peroxide may flow from the catalyst section 220 through the openings in the catalyst separation wall 222 into decontaminant air stream mixing section 230, as indicated by arrow 223.

The temperature of the product composition entering the decontaminant air stream mixing section 230 may be in the range from about 25 to about 80° C., and in one embodiment in the range from about 30 to about 70° C. The pressure in the catalyst section 220 prior to the opening or rupture of the pressure release valve or pressure release membrane in the separation wall 222 may build to a level in the range from about 2 to about 100 psi (0.14 to 6.80 atmospheres), and in one embodiment in the range from about 40 to about 80 psi (2.72 to 5.44 atmospheres). The time required for the reaction to generate sufficient pressure to open or rupture the pressure release valve or pressure release membrane in the separation wall 222 may be in the range from about 2 to about 60 seconds, and in one embodiment in the range from about 5 to about 30 seconds. The flow rate of the product composition entering the decontaminant air stream mixing section 230 from the catalyst section 220 may be in the range from about 1 to about 20 grams per minute. The amount of hydrogen peroxide reacting in the catalyst section 220 to form water and oxygen may be from about 50 to about 75 percent by weight of the hydrogen peroxide in the liquid hydrogen peroxide container 210 prior to commencing the catalytic reaction, and in one embodiment in the range from about 60 to about 70 percent by weight.

The unreacted hydrogen peroxide entering the decontaminate air stream mixing section 230 may be referred to as vaporous hydrogen peroxide (VHP). Air is drawn through the entrance 232 of the decontaminate air stream mixing section 230 by blower 250. The air flowing into the decontaminate air stream mixing section 230 may combine with the VHP to form the decontaminant air stream. As discussed above, the decontaminant air stream flows from the decontaminate air stream mixing section 230 through outlet 234 to conduit 248, from conduit 248 to blower 250 and from blower 250 through conduit 252 into the decontamination enclosure 110.

The decontaminant air stream generator 200 may be relatively small and lightweight. It may have a combined internal volume (that is, the combined internal volume of the hydrogen peroxide container 210, catalyst section 220 and mixing section 230) in the range from about 8 to about 24 ounces (236.6 to 709.8 cubic centimeters), and in one embodiment from about 12 to about 16 ounces (354.9 to 473.2 cubic centimeters). The decontaminant air stream generator 200 may have a weight in the range from about 0.5 to about 4 pounds (0.23 to 1.81 Kg), and in one embodiment in the range from about 1 to about 3 pounds (0.45 to 1.36 Kg). The decontaminant air stream generator 200 may be made of any suitable material which may include a high temperature resistant, non-catalytic metal or metal alloy. The decontaminant air stream generator 200 may be made of stainless steel, coated steal, aluminum, an aluminum alloy, anodized aluminum, and the like.

The decontamination units 100A and 100B illustrated in FIGS. 2 and 3, respectively, are the same as the decontamination unit 100 illustrated in FIG. 1 except that the decontamination units 100A and 100B employ an alternate embodiment of the decontaminant air stream generator. This is shown in FIGS. 2 and 3 as decontaminant air stream generator 200A. The decontaminant air stream generator 200A may comprise a liquid hydrogen peroxide container section 210A, a catalyst insert 220A, and a decontaminant air stream mixing section 230A. The liquid hydrogen peroxide container section 210A may contain propellant grade liquid hydrogen peroxide as discussed above. The catalyst insert 220A may comprise any of the catalysts discussed above as being suitable for decomposing hydrogen peroxide. The catalyst insert 220A may comprise a deposit, plating or coating formed on catalyst insert rod 221. The catalyst insert 220A may be relatively undersized so as to not decompose all of the hydrogen peroxide contacting the catalyst insert 220A. In operation, the catalyst insert 220A may be inserted into the liquid hydrogen peroxide in the liquid hydrogen peroxide container section 210A. An exothermic catalytic reaction occurs wherein part but not all of the hydrogen peroxide is converted to water and oxygen. The exothermic reaction heats and expands the reaction products. The resulting product composition, which includes unreacted hydrogen peroxide, expands and flows into the decontaminant air stream mixing section 230A. The unreacted hydrogen peroxide entering the decontaminant air stream mixing section 230A may be referred to as vaporous hydrogen peroxide or VHP. Air is drawn through the entrance 232A of the decontaminant air stream mixing section 230A, as indicated by arrow 231, by blower 250. The air flowing into the decontaminant air stream mixing section 230A combines with the VHP to form the decontaminant air stream. The decontaminant air stream flows from the decontaminant air stream mixing section 230A through outlet 234A to conduit 248 through conduit 248 to blower 250, and from blower 250 through conduit 252 into the decontamination enclosure 110.

The temperature of the product composition entering the decontaminant air stream mixing section 230A may be in the range from about 25 to about 80° C., and in one embodiment in the range from about 30 to about 70° C. The amount of hydrogen peroxide reacting in the decontaminant air stream generator 200A to form water and oxygen may be from about 50 to about 70 percent by weight of the hydrogen peroxide in the liquid hydrogen peroxide container section 210A prior to commencing the catalytic reaction, and in one embodiment in the range from about 60 to about 70 percent by weight.

The decontaminant air stream generator 200A may be relatively small and lightweight. It may have an internal volume in the range from about 8 to about 24 ounces (236.6 to 709.8 cubic centimeters), and in one embodiment from about 12 to about 16 ounces (354.9 to 473.2 cubic centimeters). The decontaminant air stream generator 200A may have a weight in the range from about 0.5 to about 4 pounds (0.23 to 1.81 Kg), and in one embodiment in the range from about 1 to about 3 pounds (0.45 to 1.36 Kg). The decontaminant air stream generator 200A may be made of any suitable material, for example, a high temperature resistant, non-catalytic, metal or metal alloy. The decontaminant air stream generator 200A may be made of stainless steel, coated steel, aluminum, an aluminum alloy, anodized aluminum, and the like.

The blower 250 may be relatively small and lightweight. The blower 250 may have sufficient capacity to move the decontaminant air stream through the decontamination enclosure 110 at a rate in the range from about 5 to about 40 cubic feet per minute (CFM) (0.14 to 1.13 cubic meters per minute (CMM)), and in one embodiment in the range from about 10 to about 20 CFM (0.28 to 0.57 CMM). The blower 250 may be powered by detachable solar panel 254 or by a battery. The solar panel 254 may comprise a 100 watt panel having an area of about 3 square feet (0.28 square meters). Alternatively, the blower 250 may be powered by a local source of power. The blower 250 may be made of any suitable material including stainless steel, coated steel, aluminum, an aluminum alloy, anodized aluminum, and the like. The blower 250 may be ruggedized.

The exhaust hose 280 may be made of a fabric material which may be rolled or folded during transport. The interior walls of the hose 280 may be sufficiently rough or porous to facilitate impregnation with a catalyst, and/or positioning of a filter. The fabric material may comprise a woven or non-woven fabric made of natural or synthetic fibers. Examples of suitable natural fibers that may be used may include cotton, wool, hemp, silk, and the like. The synthetic fibers may include polyester, nylon, Kevlar, Mylar, vinyl (e.g., polyvinyl chloride), polypropylene, and the like. The exhaust hose walls may be single-layered or multi-layered constructions. The multi-layered constructions may have two or more layers. The hose may have a sufficient internal cross-sectional area to permit the flow of gas out of the decontamination enclosure 110, as indicated by arrow 281, at the above indicated flow rate of about 5 to about 40 CFM and yet permit the decontamination enclosure 110 to be maintained at an internal pressure that is slightly below atmospheric pressure. The catalyst may comprise any of the catalysts discussed above for decomposing hydrogen peroxide. The catalyst may be used to convert residual hydrogen peroxide in the exhaust gas to water and oxygen. The filter may comprise a high efficiency particle air (HEPA) filter and/or a carbon filter. The filter may be used to separate residual hazardous chemical and/or biological materials from the exhaust gases flowing through the exhaust hose 280. As a result of the use of the exhaust hose 280, the exhaust gases flowing out of the exhaust hose 280, as indicated by arrow 281, may be free of or substantially free of residual hydrogen peroxide and residual hazardous chemical and/or biological materials.

The decontamination unit 100B illustrated in FIG. 3 also includes gaseous ammonia container 290 which is connected to conduit 252 through conduit 292. Regulator valve 294 is provided to regulate the flow of gaseous ammonia from the gaseous ammonia container 290 into conduit 252. The gaseous ammonia may be mixed with the decontaminant air stream in conduit 252. Although not shown in the drawings, the gaseous ammonia container 290 may also be added to the decontamination unit 100 illustrated in FIG. 1 by connecting the gaseous ammonia container 290 to conduit 252 in the same manner as illustrated in FIG. 3. The conduit 292 and regulator valve 294 may be used to provide for the flow of gaseous ammonia into the conduit 252 of the decontamination unit 100 in the same manner as illustrated in FIG. 3. The gaseous ammonia container 290 may be referred to as an ammonia cartridge. The gaseous ammonia container 290 may be made of any suitable material including stainless steel, coated steel, aluminum, an aluminum alloy, anodized aluminum, and the like. The gaseous ammonia container 290 may be ruggedized.

The decontamination units 100, 100A and 100B may be used in hostile environments such as those that may be anticipated for military applications. When intended for use in such hostile environments, the collapsible enclosure 110, and in one embodiment also the decontaminant air stream generator 200 or 200A, blower 250, exhaust hose 280, and/or gaseous ammonia container 290, as well as the conduits used to connect the foregoing, may be constructed using any material that is sufficient to provide the required properties of strength and lightweight, as well as ruggedization. Ruggedization may include providing resistance to hot and cold temperatures, solar radiation, rain, fungus, salt, fog, sand and/or dust, resistance to vibration and shock, as well as resistance to CBRN contaminants. This may involve construction of the foregoing equipment in compliance with military standard MIL-STD-810. The foregoing equipment may be constructed of materials capable of withstanding exposure to the decontaminants that may be used in the decontamination process as well as the contaminants that may be encountered.

The decontaminant air stream comprises air and VHP, and optionally gaseous ammonia. When the decontaminant air stream flows into the decontamination enclosure 110 and contacts the contaminated articles, the process may be regarded as a dry process characterized by the absence of condensate formation on the surfaces of the contaminated articles being decontaminated. Alternatively, the process may be regarded as a wet process characterized by the formation of a condensate in the form of a liquid film on the surfaces of the contaminated articles. The liquid film may have a film layer thickness in the range up to about 20 microns, and in one embodiment up to about 10 microns, and in one embodiment up to about 5 microns, and in one embodiment up to about 1 micron. The film layer may be referred to as a microcondensate layer of hydrogen peroxide. The addition of ammonia may be used to control the pH of the decontaminant air stream.

VHP, when used in combination with ammonia gas, may be referred to as modified VHP or mVHP. The volumetric ratio of VHP to ammonia gas may be in the range from about 1:1 to about 1:0.0001. VHP and mVHP may be effective microbial and chemical decontaminants because they may provide a broad spectrum of activity against a wide variety of pathogenic microorganisms and chemical pathogenic agents, such as hard to destroy spores of *Bacillus stearothermophilus*, *Bacillus anthracis*, smallpox virus, and the like. They may be also effective at or close to room temperature (e.g., about 15 to about 30° C.), making them suitable for use in the decontamination enclosure 110 with little or no heating. VHP and mVHP may have good material compatibility, rendering them safe for use with a variety of equipment and materials, including electronic equipment, and the like. VHP may degrade to water and oxygen over time, which may not be harmful to a person subsequently opening the decontamination enclosure 110. Low levels of hydrogen peroxide (for example, about 1 ppm, or less) that may remain in the decontamination enclosure 110 after the decontamination process has been completed may not be considered to pose a risk to a person opening the decontamination enclosure 110.

The progress of the decontamination process may be monitored using one or more decontamination or sterilization indicators. These indicators may contain a biological indicator. The biological indicator may comprise one or more test organisms which may be more resistant to the decontamination process than the organisms to be destroyed by the decontamination process. The test organism may be placed in contact with an incubation medium to determine whether the decontamination process was effective.

The temperature of the decontaminant air stream entering the decontamination enclosure 110, as well as the temperature within the decontamination enclosure 110, may be in the range from about 10° C. to about 80° C., and in one embodiment in the range from about 15° C. to about 50° C., and in one embodiment in the range from about 15° C. to about 30° C. The relative humidity of the decontaminant air stream entering the decontamination enclosure 110 may be in the range from about 0 to about 50%, and in one embodiment in the range from about 20 to about 40% by volume. The term "relative humidity" is used herein to refer to the ratio of the partial pressure of water vapor in the decontaminant air stream to the saturated vapor pressure of water at the temperature of the decontaminant air stream expressed in terms of percentage. The concentration of the VHP in the decontaminant air stream entering the decontamination enclosure 110 may be in the range from about 0.01 to about 2% by volume, and in one embodiment in the range from about 0.01 to about 1.5% by volume, and in one embodiment in the range from about 0.01 to about 1% by volume, and in one embodiment in the range from about 0.01 to about 0.5% by volume, and in one embodiment in the range from about 0.02 to about 0.2% by volume, and in one embodiment in the range from about 0.02 to about 0.05% by volume. When the VHP is used in combination with ammonia, the concentration of ammonia in the decontaminant air stream entering the decontamination enclosure 110 may be in the range from about 0.001 to about 0.01% by volume, and in one embodiment in the range from about 0.003 to about 0.005% by volume. The gas flow rate through the decontamination enclosure 110 may be in the range from about 5 to about 40 CFM (0.14 to 1.13 CMM), and in one embodiment in the range from about 10 to about 20 CFM (0.28 to 0.57 CMM). The operating pressure within the decontamination enclosure 110 may be slightly negative to prevent the leakage of contaminants and decontaminants from the decontamination enclosure 110. The internal pressure may be up to about 10 inches of water, and in one embodiment in the range from about 1 to about 5 inches of water, below atmospheric pressure.

The contaminated articles may be contaminated with any contaminant. The articles to be decontaminated may comprise any article that may be stored in the decontamination enclosure 110. These may include military weapons, clothing, body armor, as well as sensitive equipment such as computers, test equipment, optical devices, electronic devices, communications equipment, and the like. These may include radio headsets and night vision goggles, as well as other small but high value pieces of equipment. The contaminant may comprise one or more chemical, biological, radiological and/or nuclear (CBRN) warfare agents.

Different levels of decontamination may be accomplished within the decontamination enclosure 110. As used herein, the term "decontamination," may encompass both microbial decontamination as well as chemical decontamination—the destruction of chemical agents, or their conversion to harmless or odorless compounds. Decontamination may also encompass the neutralizing of unpleasant odors, such as tobacco smoke, perfume, or body odor residues, and odors and dampness due to molds. "Microbial decontamination" may be used herein to encompass the destruction of biological contaminants, specifically, living microorganisms, and also the destruction or inactivation of pathogenic forms of proteinaceous-infectious agents (prions). The term microbial decontamination may encompass sterilization, the highest level of biological contamination control, which connotes the destruction of all living microorganisms. The term may also include disinfection, the destruction of harmful microorganisms, and sanitizing, which connotes being free from germs. "Chemical decontamination" is intended to encompass the destruction of pathogenic chemical agents or their conversion to less harmful or odiferous species.

Exemplary biological contaminants which may be destroyed in the decontamination process include bacterial spores, vegetative bacteria, viruses, molds, and fungi. Some of these may be capable of killing or causing severe injury to mammals, particularly humans. Included among these are viruses, such as *equine encephalomyelitis* and smallpox, the coronavirus responsible for Severe Acute Respiratory Syndrome (SARS); bacteria, such as those which cause plague (*Yersina pestis*), anthrax (*Bacillus anthracis*), and tularemia (*Francisella tularensis*); and fungi, such as coccidioidomycosis; as well as toxic products expressed by such microorganisms; for example, the botulism toxin expressed by the common *Clostridium botulinium* bacterium.

Also included are the less harmful microorganisms, such as those responsible for the common cold (rhinoviruses), influenza (orthomyxoviruses), skin abscesses, toxic shock syndrome (*Staphylococcus aureus*), bacterial pneumonia (*Streptococcus pneumoniae*), stomach upsets (*Escherichia coli*, Salmonella), and the like.

Exemplary pathogenic chemical agents may include substances which are often referred to as chemical warfare agents, such as poison gases and liquids, particularly those which are volatile, such as nerve gases, blistering agents (also known as vesicants), and other extremely harmful or toxic chemicals. As used herein, the term "chemical pathogenic agent" is intended to include only those agents which are effective in relatively small dosages to substantially disable or kill mammals and which can be degraded or otherwise rendered harmless by a process which includes oxidation.

Exemplary chemical pathogenic agents may include choking agents, such as phosgene; blood agents, which act on the enzyme cytochrome oxidase, such as cyanogen chloride and hydrogen cyanide; incapacitating agents, such as 3-quinuclidinyl benzilate ("BZ"), which blocks the action of acetylcholine; vesicants, such as di(2-chloroethyl) sulfide (mustard gas or "HD") and dichloro(2-chlorovinyl)arsine (Lewisite); nerve agents, such as ethyl-N, N dimethyl phosphoramino cyanidate (Tabun or agent GA), o-ethyl-S-(2-diisopropyl aminoethyl) methyl phosphono-thiolate (agent VX), isopropyl methyl phosphonofluoridate (Sarin or Agent GB), methylphosphonofluoridic acid 1,2,2-trimethylpropyl ester (Soman or Agent GD).

While the disclosed invention has been explained in relation to various detailed embodiments, it is to be understood that various modifications thereof may become apparent to those skilled in the art upon reading the specification. Therefore, it is to be understood that the invention specified herein is intended to include such modifications as may fall within the scope of the appended claims.

The invention claimed is:

1. A decontamination unit, comprising:
    a collapsible enclosure equipped with a gas inlet and a gas outlet, the collapsible enclosure when erected being suitable for providing a decontamination enclosure for containing articles to be decontaminated, the collapsible enclosure when collapsed being suitable for being transported;
    a decontaminant air stream generator which comprises a liquid hydrogen peroxide container, a catalyst section containing a catalyst therein, and a decontaminant air stream mixing section, the liquid hydrogen peroxide container including a liquid hydrogen peroxide separation wall which separates the liquid hydrogen peroxide container from the catalyst section, the liquid hydrogen peroxide separation wall comprising one or more passageways for permitting liquid hydrogen peroxide to flow from the liquid hydrogen peroxide container to the catalyst section where the liquid hydrogen peroxide contacts the catalyst within the catalyst section or being made of a frangible material which when broken permits liquid hydrogen peroxide to flow from the liquid hydrogen peroxide container to the catalyst section where the liquid hydrogen peroxide contacts the catalyst within the catalyst section, the generator being adapted for catalytically converting part of the liquid hydrogen peroxide to water and oxygen in an exothermic reaction and for vaporizing part of the liquid hydrogen peroxide to form vaporous hydrogen peroxide, the generator including an inlet adapted for permitting air to flow into the decontaminant air stream mixing section in contact with the vaporous hydrogen peroxide and an outlet adapted for permitting a decontaminant air stream comprising the air and vaporous hydrogen peroxide to flow out of the decontaminant air stream mixing section;
    a blower adapted to be connected to the generator outlet and the collapsible enclosure gas inlet, the blower being suitable for forcing the flow of the decontaminant air stream from the generator into the collapsible enclosure; and
    an exhaust hose adapted to be attached to the collapsible enclosure gas outlet, the exhaust hose comprising an interior wall impregnated with a catalyst for converting hydrogen peroxide to water and oxygen, and/or the exhaust hose comprising a biological and/or chemical hazard filter to separate hazardous chemical and/or biological materials from exhaust gas flowing in the exhaust hose.

2. The decontamination unit of claim 1 wherein the collapsible enclosure comprises a floor and side walls made of a fabric or film.

3. The decontamination unit of claim 1 wherein the collapsible enclosure includes an interior support frame.

4. The decontamination unit of claim 1 wherein the collapsible enclosure is erected to form the decontamination enclosure, the decontamination enclosure having an internal volume in the range from about 0.5 to about 30 cubic meters.

5. The decontamination unit of claim 1 wherein the collapsible enclosure is ruggedized.

6. The decontamination unit of claim 1 wherein the catalyst section includes a catalyst separation wall which separates the catalyst section from the decontaminant air stream mixing section, the catalyst separation wall including one or more openings adapted to permit the flow of reaction products from the catalyst section into the decontaminant air stream mixing section and a pressure release valve or a pressure release membrane positioned in the one or more openings.

7. The decontamination unit of claim 1 wherein the blower is adapted to be connected to the generator outlet by a first conduit and to the collapsible enclosure gas inlet by a second conduit.

8. The decontamination unit of claim 1 wherein the blower is powered by a solar cell or a battery.

9. The decontamination unit of claim 7 wherein the decontamination unit further comprises a gaseous ammonia container, the gaseous ammonia container being adapted to be connected to the first conduit or the second conduit to permit the gaseous ammonia to flow into the first or second conduit in contact with the decontaminant air stream.

10. The decontamination unit of claim 1 wherein the generator is ruggedized.

11. The decontamination unit of claim 9 wherein the collapsible enclosure, generator, blower, exhaust hose and/or gaseous ammonia container are ruggedized.

12. A process for operating the decontamination unit of claim 1, comprising;
    erecting the collapsible enclosure to form a decontamination enclosure suitable for receiving articles to be decontaminated;
    connecting the blower to the gas inlet of the enclosure;
    connecting the blower to the generator;
    connecting the exhaust hose to the gas outlet of the enclosure;

placing one or more contaminated articles in the enclosure;
generating a decontaminant air stream comprising air and vaporous hydrogen peroxide in the generator;
flowing the decontaminant air stream into the enclosure;
contacting the contaminated articles in the enclosure with the decontaminant air stream to decontaminate the contaminated articles;
flowing gas from the enclosure through the exhaust hose;
opening the enclosure; and
removing decontaminated articles from the enclosure.

13. The process of claim 12 wherein the decontaminant air stream further comprises ammonia.

14. The process of claim 12 wherein the contaminated articles comprise one or more of military weapons, clothing, body armor, radio headsets, night vision goggles, computers, test equipment, optical devices, electronic devices and/or communications equipment.

15. The process of claim 12 wherein the contaminated articles are contaminated with one or more chemical, biological, radiological and/or nuclear warfare agents.

16. The process of claim 12 wherein the contaminated articles are contaminated with one or more bacterial spores, vegetative bacteria, viruses, molds and/or fungi.

17. The process of claim 12 wherein the contaminated articles are contaminated with one or more pathogenic chemical agents.

18. The process of claim 12 wherein the step of contacting the contaminated articles with the decontaminant air stream comprises a dry process characterized by the absence of condensate formation on the surface of the contaminated articles being decontaminated.

19. The process of claim 12 wherein the step of contacting the contaminated articles with the decontaminant air stream comprises a wet process characterized by the formation of condensate on the surface of the contaminated articles being decontaminated.

20. The process of claim 19 wherein the condensate comprises hydrogen peroxide.

21. The decontamination unit of claim 1 wherein the catalyst section comprises a catalyst insert.

* * * * *